(12) United States Patent
Kojima (10) Patent No.: US 7,498,464 B2
(45) Date of Patent: Mar. 3, 2009

(54) METHOD AND APPARATUS FOR SYNTHESIZING UREA

(75) Inventor: Yasuhiko Kojima, Narashino (JP)

(73) Assignee: Toyo Engineering Corporation, Tokyo (JP)

( * ) Notice: Subject to any disclaimer, the term of this patent is extended or adjusted under 35 U.S.C. 154(b) by 2 days.

(21) Appl. No.: 11/421,002

(22) Filed: May 30, 2006

(65) Prior Publication Data

US 2006/0270872 A1    Nov. 30, 2006

(51) Int. Cl.
*C07C 273/04* (2006.01)
(52) U.S. Cl. .............................. 564/67; 564/68; 564/70; 564/71; 564/72
(58) Field of Classification Search .................. 564/67, 564/68, 70, 71, 72
See application file for complete search history.

(56) References Cited

U.S. PATENT DOCUMENTS 4,572,830 A * 2/1986 Biermans et al. ............. 423/659
6,632,967 B2 * 10/2003 Scholten et al. ............... 564/67

FOREIGN PATENT DOCUMENTS

| EP | 0 114 442 A1 | 8/1984 |
| JP | 59-133451 | 7/1984 |
| JP | 10-182586 | 7/1998 |
| WO | WO 01/3078 A1 | 5/2001 |

* cited by examiner

*Primary Examiner*—Peter G O'Sullivan
(74) *Attorney, Agent, or Firm*—Knobbe Martens Olson & Bear, LLP (57) ABSTRACT

In a process and an apparatus for synthesizing urea which synthesize urea from ammonia and carbon dioxide, the operating condition can be grasped easily and with good accuracy. A process for synthesizing urea which includes: a reaction step of obtaining a urea synthesis solution which contains urea, unreacted ammonia, unreacted carbon dioxide and water by causing ammonia and carbon dioxide to react with each other; a stripping step of separating a gas mixture containing the unreacted ammonia and the unreacted carbon dioxide by stripping the urea synthesis solution by using at least a portion of raw material carbon dioxide; a condensing step of obtaining a condensed liquid by condensing the gas mixture in an absorbing medium while cooling the gas mixture; a recycling step of recycling the condensed liquid to the reaction step; and a step of measuring the density of the condensed liquid online. An apparatus for carrying out this process is provided.

17 Claims, 5 Drawing Sheets

METHOD AND APPARATUS FOR SYNTHESIZING UREA

BACKGROUND

1. Field of the Invention

The present invention relates to a method and an apparatus for synthesizing urea which synthesize urea by using ammonia and carbon dioxide as raw materials.

2. Background of the Invention

In a urea manufacturing plant, it is important to grasp the operating condition of the plant although there are differences in urea synthesis conditions, such as the urea synthesizing pressure, the urea synthesizing temperature, N/C (the mole ratio of an ammonia component to a carbon dioxide component) and H/C (the mole ratio of a water component to a carbon dioxide component). In particular, N/C is an important parameter for the operation of a urea synthesizing plant and, therefore, it is useful to grasp N/C.

For example, Patent Document 1 discloses measuring the density of a urea synthesis solution in real time at the outlet of a urea synthesizing zone and determining the value of N/C of the synthesis solution from the value of obtained density.

Patent Document 2 describes measuring the compositions of various streams of a urea synthesizing process by use of ultrasonic waves.

Patent Document 3 describes finding the compositions of aqueous solutions of $NH_3$ and $CO_2$ on the basis of measured values of concentration and saturation temperature and using a vibration type densimeter for this concentration measurement.

Patent Document 1: Japanese Patent No. 3270700

Patent Document 2: International Publication WO 01/30748A1

Patent Document 3: Japanese Patent Laid-Open No. 59-133451

SUMMARY OF THE INVENTION

The method for determining the composition and, particularly, N/C of a urea synthesis solution by using density is excellent in that measurements can be made simply and in real time.

In the conventional method, however, a urea synthesis solution at the outlet of a synthesis reactor was an object of measurement in order to know the operating condition, particularly, N/C of a plant. In this case, a urea synthesis solution at the outlet of a synthesis reactor may sometimes be a gas-liquid two-phase flow. It is difficult to measure the density of a gas-liquid two-phase flow with good accuracy. That is, in the conventional method, it is not always easy to measure the density with good accuracy. As a result, it has not always been easy to grasp the operating condition, particularly, N/C of a plant with good accuracy.

An object of the present invention is to provide a method and an apparatus for synthesizing urea which avoid that a gas-liquid two-phase flow becomes an object of measurement, and enable good-accuracy density measurements to be easily performed, thereby enable the operating condition to be easily grasped with good accuracy.

The present invention provides a method for synthesizing urea, which includes:

a reaction step of obtaining a urea synthesis solution which contains urea, unreacted ammonia, unreacted carbon dioxide and water by causing ammonia and carbon dioxide to react with each other;

a stripping step of separating a gas mixture containing the unreacted ammonia and the unreacted carbon dioxide by stripping the urea synthesis solution using at least a part of raw material carbon dioxide;

a condensing step of obtaining a condensed liquid by condensing the gas mixture in an absorbing medium while cooling the gas mixture;

a recycling step of recycling the condensed liquid to the reaction step; and a step of measuring the density of the condensed liquid online.

Further, in the above-described method, it is preferred that the temperature of the condensed liquid be measured online and that an N/C value of the condensed liquid be determined using measured values of the temperature and the density.

Further, it is preferred that in this method, an N/C value in the reaction step be calculated using the N/C value of the condensed liquid.

Further, it is preferred that in this method, the N/C value in the reaction step be controlled to a predetermined value by adjusting the flow rate of raw material ammonia and/or raw material carbon dioxide.

It is preferred that a noncontact type density meter be used to measure the density.

It is preferred that the noncontact type density meter be a radiation type density meter.

The present invention provides an apparatus for synthesizing urea, which includes:

a synthesis reactor for obtaining a urea synthesis solution which contains urea, unreacted ammonia, unreacted carbon dioxide and water by causing ammonia and carbon dioxide to react with each other;

a stripper for separating a gas mixture containing the unreacted ammonia and the unreacted carbon dioxide by stripping the urea synthesis solution using at least a part of raw material carbon dioxide;

a condenser for obtaining a condensed liquid by condensing the gas mixture in an absorbing medium while cooling the gas mixture;

recycling means for recycling the condensed liquid to the synthesis reactor; and a density meter for measuring the density of the condensed liquid online.

It is preferred that the above-described apparatus for synthesizing urea further includes a thermometer for measuring the temperature of the condensed liquid online and calculating means for calculating an N/C value of the condensed liquid using measured values of the temperature and the density.

It is preferred that this apparatus for synthesizing urea further includes calculating means for calculating an N/C value in the synthesis reactor using the N/C value of the condensed liquid.

It is preferred that this apparatus for synthesizing urea further includes control means for controlling the N/C value in the reaction step to a predetermined value by adjusting the flow rate of raw material ammonia and/or raw material carbon dioxide.

It is preferred that the density meter is a noncontact type density meter.

It is preferred that the noncontact type density meter is a radiation type density meter.

According to the present invention, there are provided a method and an apparatus for synthesizing urea which avoid that a gas-liquid two-phase flow becomes an object of measurement, and enable good-accuracy density measurements to be easily performed, thereby enable the operating condition to be easily grasped with good accuracy.

A: Synthesizing reactor
B: Condenser
C: Stripper
D: Scrubber
E: Ejector
F: Gas-liquid separator
G: Ammonia preheater
I: Density meter
1: Raw material ammonia
2: Raw material carbon dioxide
3: Fluid at condenser outlet (before gas-liquid separation)
4: Synthesis solution at synthesis reactor outlet
5: Outlet gas at stripper top
6: Liquid obtained from condenser (after gas-liquid separation)
8: Liquid at ejector outlet
10: Liquid at stripper outlet
11: Recycled carbamate liquid
12: Gas obtained from condenser
13: Cooling medium at condenser inlet (boiler water)
14: Cooling medium at condenser outlet (boiler water and steam)
15: Steam for stripper heating
16: Condensed water at stripper outlet

DETAILED DESCRIPTION OF THE INVENTION

In the present invention, the density of a condensed liquid obtained in the condenser is measured online. Because the condensed liquid is not a two-phase flow, it is possible to easily measure the density with good accuracy.

Furthermore, it is possible to measure the temperature of the condensed liquid online and determine the N/C of the condensed liquid using the density and temperature of the condensed liquid. As a result of this, the N/C of the condensed liquid can be monitored substantially in real time.

Furthermore, it is possible to calculate the N/C in the reaction step or in the synthesis reactor using the N/C of the condensed liquid. For this purpose, it is only necessary that the material balance of an ammonia component and a carbon dioxide component in the synthesis reactor be calculated, and therefore, it becomes possible to monitor the N/C in the reaction step or in the synthesis reactor substantially in real time.

Furthermore, it is possible to control the N/C in the reaction step or in the synthesis reactor to a predetermined value by adjusting the flow rate of the raw material ammonia and/or the raw material carbon dioxide. In a case where the density of the liquid at the outlet of the synthesis reactor is measured and the N/C in the synthesis reactor found from this density is controlled, even when the a feed rate of raw material is manipulated, the response time becomes long because the residence time in the synthesis reactor is as long as about 30 minutes, for example. However, by using the N/C in the synthesis reactor calculated on the basis of the density of the condensed liquid (the fluid on the inlet side of the synthesis reactor) as an object of control, it is possible to shorten the response time without being affected by the residence time.

N/C means the mole ratio of an ammonia component to a carbon dioxide component, and H/C means the mole ratio of a water component to a carbon dioxide component. The ammonia component includes ammonia which has been converted into ammonium carbamate and ammonia which has been converted into urea in addition to ammonia which exists actually. Therefore, the molar quantity of the ammonia component is a total amount of twice the molar quantity of urea, twice the molar quantity of ammonium carbamate and the molar quantity of ammonia. The carbon dioxide component includes carbon dioxide which has been converted into ammonium carbamate and carbon dioxide which has been converted into urea in addition to carbon dioxide which exists actually. Therefore, the molar quantity of the carbon dioxide component is a total amount of the molar quantity of urea, the molar quantity of ammonium carbamate and the molar quantity of carbon dioxide. The water component is actually-existing water except the water which has been formed as a result of the urea synthesis. Therefore, the molar quantity of the water component is a value obtained by deducting the molar quantity of urea from the molar quantity of water.

The correlation between the temperature t (° C.) and density d (kg/m$^3$) of the liquid obtained from the condenser (the condensed liquid), which is supplied to the synthesis reactor, and the N/C value of the urea synthesis solution obtained in the synthesis reactor will be described below.

The N/C of the liquid obtained from the condenser can be determined by using the above-described t and d and by use of the following simplified formula.

$$N/C = C_1 d + C_2 t + C_3$$

(where $C_1$, $C_2$ and $C_3$ are constants)

By using the flow rates of the ammonia and carbon dioxide which are supplied to the synthesis reactor separately from the condensed liquid, in addition to the N/C of the condensed liquid thus found, it is possible to calculate the N/C of the urea synthesis solution.

If the temperature and density of the liquid obtained from the condenser are measured online and an N/C value of the urea synthesis solution is calculated on the basis of these temperature and density, it is possible to improve the controllability of the control for keeping the operation conditions of the synthesis reactor within given operation ranges. For example, the flow rate of the ammonia component supplied to the synthesis reactor is calculated using the calculated N/C value of the urea synthesis solution and the flow rate of the raw material ammonia supplied to the apparatus for synthesizing urea is adjusted so that the flow rate of the ammonia component supplied to the synthesis reactor becomes a flow rate corresponding to a predetermined N/C value, whereby it becomes easy to control the N/C in the synthesis reactor to a predetermined value.

An absorbing medium to be used in the condenser is supplied to the apparatus for synthesizing urea which is provided with the synthesis reactor, the stripper, the condenser and the recycling means. A recovered liquid (an aqueous solution of ammonium carbamate) obtained in a recovery apparatus which is provided separately from the apparatus for synthesizing urea can be used as this absorbing medium.

It is possible to get to know not only the N/C in the synthesis reactor, but also the H/C by measuring the flow rate of the recovered liquid online in addition to the above-described calculation of the NIC in the synthesis reactor. Furthermore, it is possible to estimate the material balance of the apparatus for synthesizing urea in real time. As a result, it is possible to operate the apparatus for synthesizing urea in a stabler manner and with better controllability. Incidentally, ammonia and carbon dioxide may be supplied to the apparatus for synthesizing urea in addition to this absorbing medium (the recovered liquid), and their feed rates are monitored in real time as required and used in the calculation of the N/C value of the urea synthesis solution and also used in the calculation of the material balance of the apparatus for synthesizing urea.

The urea synthesis solution may sometimes contain gases, that is, the urea synthesis solution may be a gas-liquid two-phase flow. In the present invention, however, the density of the liquid phase obtained from the condenser and recycled to the synthesis reactor is measured. Therefore, measurement accuracy is not affected by the presence of a gas phase.

Further, as in the case of the schemes shown in FIGS. 1 to 4, which will be described later, when the synthesizing pressure is controlled by the gas discharged from the condenser, the synthesizing pressure is greatly affected by the N/C in the condenser. Therefore, the control of the urea synthesizing pressure becomes easy by measuring the density and temperature of the condensed liquid and calculating the N/C in the condenser.

Besides, even in a case where the condensed liquid is not supplied to the synthesis reactor due to some abnormality or operation mistakes, this situation can be detected immediately by installing the density meter in the outlet piping of the condenser. If the outlet of the synthesis reactor is monitored instead of the inlet thereof, due to a delay in response, it may take time until this situation becomes detected.

As the density meter which measures the density of the condensed liquid, it is preferable to use a noncontact type density meter capable of measuring density without coming into contact with the urea synthesis solution from the standpoint of preventing corrosion and clogging by the urea synthesis solution.

A radiation type density meter is preferably used as the noncontact type density meter. A commercially available radiation type density meter is sufficient, and for example, DENSART Density Series D-3000 (trade name) made by Ohmart Corporation and LB491 (trade name) made by Berthold Technologies GmbH & Co. KG can be mentioned. In a radiation type density meter, radiation ray is irradiated from one side of a pipe and received in a receiving section on the other side, and density is calculated from the intensity of the received radiation ray. For example, a radiation type density meter can be attached by a clamp to the outside of a pipe through which a liquid obtained from a condenser flows.

It is also possible to use a vibration type density meter. In the case of a vibration type, it is possible to appropriately provide devices ancillary to the density meter, such as a branch pipe to take out a sample liquid, and a device for diluting or cooling the sample liquid. A vibration type density meter is a contact type which uses Corioris force, and commercially available products such as Micromotion E Series (trade name) made by Oval Corporation may be used.

The temperature of the liquid obtained from the condenser and recycled to the synthesis reactor, can be measured by use of a publicly known thermometer, such as a thermocouple and a resistance thermometer bulb installed in a line through which this liquid flows or in the condenser.

Publicly known calculating means, such as a distributed control system and a computer, can be used as the calculating means (first calculating means) for calculating the N/C of the condensed liquid from measured values of the temperature and density of the condensed liquid and calculating means (second calculating means) for calculating the N/C value in the synthesis reactor using the N/C value of the condensed liquid.

The control means for controlling the N/C in the above-described reaction step to a predetermined value by adjusting the flow rate of the raw material ammonia and/or the raw material carbon dioxide, which are supplied to the apparatus for synthesizing urea, can be formed by appropriately using publicly known calculating means, such as a distributed control system and a computer, and publicly known flow rate regulating means, such as an automatic flow rate regulating valve which adjusts the flow rate of the raw material ammonia and an automatic flow rate regulating valve which adjusts the flow rate of the raw material carbon dioxide.

A single distributed control system or computer may serve as two or more of the first calculating means, the second calculating means and the calculating means provided in the control means.

Instrumentation equipment, such as instrument wiring and a signal converter, may be appropriately provided.

Although the present invention will be described below by using drawings, the invention is not limited thereby. In FIGS. 1 to 4 are shown positional relationships of each piece of the apparatus in the vertical direction.

Figure 1:
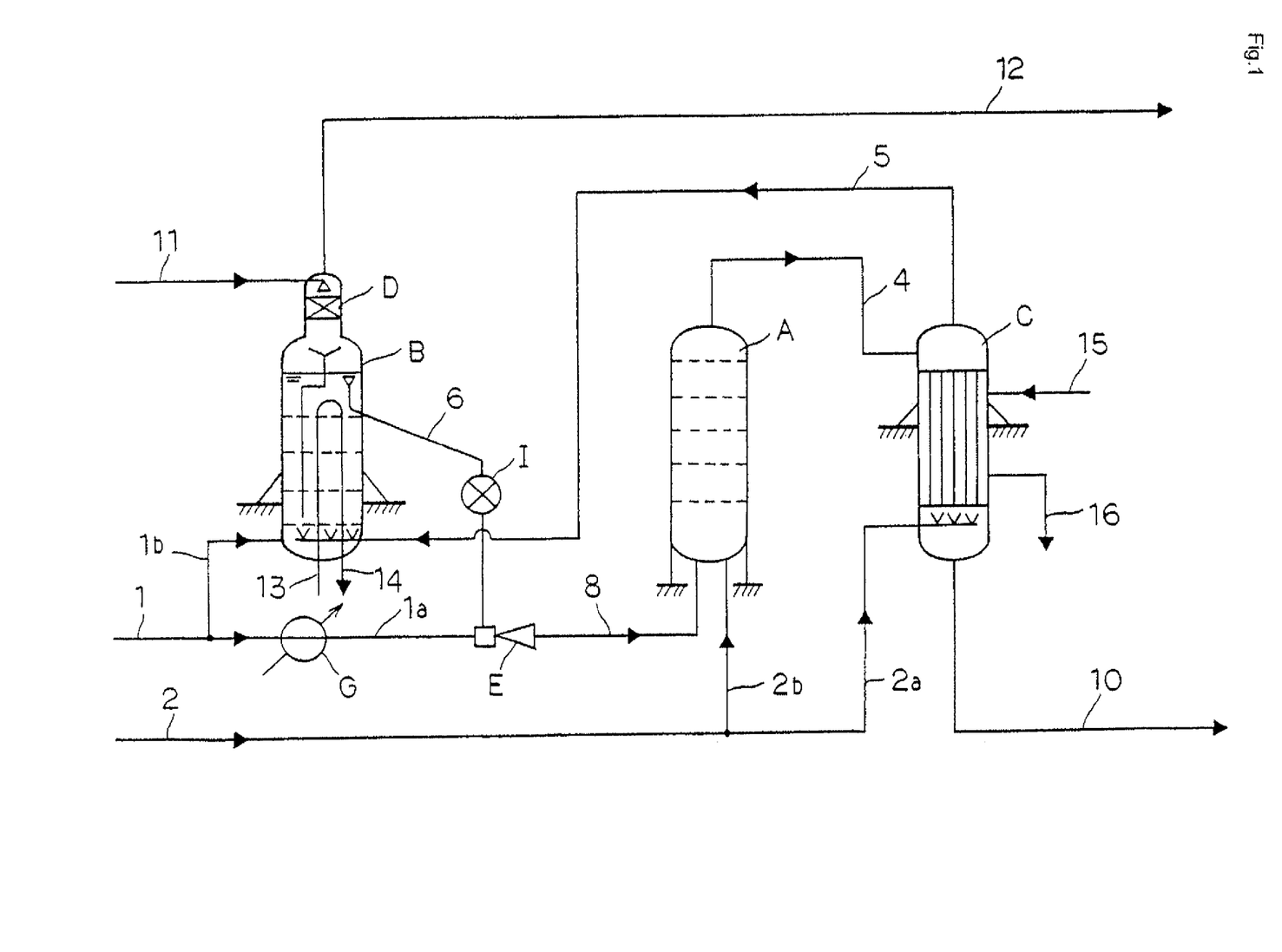
FIG. 1 is a flow diagram which illustrates an embodiment of an apparatus for synthesizing urea of the present invention.

FIG. 1 is a flow diagram which shows an embodiment of an apparatus for synthesizing urea of the present invention. This apparatus has a synthesis reactor A, a condenser B, a stripper C which treats unreacted components in a synthesis solution 4 at the outlet of the synthesis reactor A, a scrubber D for causing uncondensed gases to be absorbed, which is formed integrally with the condenser B, and an ejector E for pressurizing.

Although a vertical submerged condenser is used here as the condenser, this is not necessary. The condenser may be a horizontal type, and in addition to the submerged type, it is also possible to use a vertical falling liquid film condenser in which the condensed liquid passes through tubes, a horizontal kettle condenser (shown in FIG. 2), a horizontal submerged condenser (shown in FIGS. 3 and 4) or the like.

These apparatuses may be separately installed, or as required, the synthesis reactor and the condenser, or the condenser and the scrubber, etc. may be combined. Also, the synthesis reactor may be either a vertical type or a horizontal type, and is appropriately selected from the standpoint of economical efficiency and the like.

In the synthesis reactor, as shown by Formula 1 and Formula 2 below, ammonium carbamate (hereinafter referred to as carbamate in some cases) is formed by a reaction between ammonia and carbon dioxide, and urea is formed by the dehydration of the formed carbamate. The reaction rate of the formation of carbamate is high, and the formation reaction of urea by the dehydration of carbamate is an equilibrium reaction. These reactions may occur in the condenser.

2NH$_3$+CO$_2$→NH$_2$CO$_2$NH$_4$ (Exothermic reaction)   Formula 1

NH$_2$CO$_2$NH$_4$⇌CO(NH$_2$)$_2$+H$_2$O (Endothermic reaction)   Formula 2

Liquid ammonia 1 which is a raw material is pressurized to a desired pressure by an ammonia pump (not shown in the figure) and a portion 1a of the liquid ammonia is heated by a heat exchanger G and supplied to the ejector E. A liquid 6 obtained from the condenser B is supplied to the ejector E and pressurized. On the other hand, gaseous carbon dioxide 2 which is a raw material is pressurized to a desired pressure by a carbon dioxide compressor which is not shown in the figure and the greater part 2a of the carbon dioxide is supplied to the stripper C. The remaining portion 2b of carbon dioxide is supplied to the synthesis reactor A for the purpose of controlling the temperature of the synthesis reactor and to supply oxygen for corrosion prevention. As the oxygen for corrosion prevention, air for corrosion prevention may be supplied to the first stage suction side or to the middle stage of the carbon dioxide compressor (not shown in the figure). As the heat exchanger G, it is possible to appropriately adopt a publicly known heat exchanger having a structure capable of heating the raw material ammonia. As a heat medium for heating in the heat exchanger G, it is possible to appropriately use a fluid having a desired temperature level.

A very small portion of the whole raw material ammonia may be supplied as ammonia for corrosion protection 1b to the condenser for the corrosion prevention of welds of a tubesheet of the condenser. The feed line for this raw material ammonia 1b is not always necessary.

A synthesis solution 8 containing the ammonia from the ejector E is supplied to the synthesis reactor as in the case of carbon dioxide.

This ejector E constitutes the recycling means which recycles the liquid 6 obtained from the condenser B to the synthesis reactor A. In FIG. 1, the recycling means has a down pipe having an inlet below a gas-liquid interface, which is provided in the interior of the condenser, the ejector E and the lines 6 and 8, and a density meter I is provided in the line 6. Although, for the recycling, it is also possible to use other pressurizing means such as a pump in place of the ejector, the ejector is preferable because of its simple construction and excellent endurance and maintainability. As an operating condition (a pressure difference between the lines 6 and 8) of the ejector, it is possible to set not less than 0.2 MPa but not more than 1 MPa, for example.

The recycling means need not have pressurizing means such as an ejector. In some arrangements of the equipment, it is possible to recycle the liquid 6 to the synthesis reactor by gravity alone. However, if pressurizing means which raises the pressure of the liquid 6 is provided, it is possible to install the condenser in a relatively low position, in particular near the ground surface, and hence this is preferable from the standpoint of installation work and maintenance.

In the synthesis reactor, the urea synthesizing reaction proceeds preferably near to an equilibrium synthesis rate and urea is synthesized. In the synthesis reactor, it is preferred that urea be synthesized at a pressure of not less than 13 MPaG but not more than 25 MPaG (G in the pressure unit means gauge pressure), at a temperature of not less than 170° C. but not more than 210° C., at N/C of not less than 3.0 but not more than 4.5, at H/C of not more than 1.0, and for a residence time of not less than 10 minutes but not more than 40 minutes.

The synthesis temperature can be controlled, for example, by the preheating temperature of the ammonia 1a which drives the ejector and/or the amount of the carbon dioxide 2b supplied to the synthesis reactor A. The N/C of the synthesis solution 4 obtained in the synthesis reactor A can be determined from the density and temperature of the synthesis solution 6 measured by the density meter I and a thermometer which is not shown in the figure. This thermometer can be provided in the piping where the density meter is provided, preferably in a position close to the density meter. The adjustment of N/C can be performed, for example, by adjusting the amount of the raw material ammonia 1a supplied to the ejector E, and for this purpose, the amount of the raw material ammonia 1 can be adjusted. H/C is often determined, in the recovery apparatus (not shown in FIG. 1) for recovering unreacted substances (ammonia and carbon dioxide) which are discharged from the synthesis reactor A, by the amount of the water necessary for the absorption of the unreacted substances. Because water impedes the urea synthesizing reaction in terms of equilibrium (in terms of synthesis equilibrium, the lower H/C, the better), it is preferred that the amount of the water supplied to this recovery apparatus be a requisite minimum. The recovery apparatus will be described later.

In the synthesis reactor, the urea synthesis rate based on carbon dioxide is determined by a chemical equilibrium and is not less than 60% but not more than 75% or so in the N/C range of not less than 3.0 but not more than 4.5.

The urea synthesis rate based on carbon dioxide is the ratio (the carbon dioxide conversion ratio) of the number of moles of the carbon dioxide which has been converted into urea among the supplied carbon dioxide to the number of moles of the carbon dioxide supplied to the equipment or zone which is the object of consideration, and this ratio is usually expressed by %.

It is preferable to set the synthesis pressure at not less than 13 MPaG from the standpoint that it is possible to adopt an operating pressure having a margin for a synthesis equilibrium pressure at temperatures preferable for the synthesis of urea (not less than 170° C.) and from the standpoint that a decrease in the synthesis rate due to vaporization is prevented. It is preferable to set the synthesis pressure at not more than 25 MPaG from the standpoint that it is possible to reduce the energy for pressurizing the raw material ammonia, the raw material carbon dioxide and a recovered liquid 11 and also in terms of equipment cost.

It is preferable to set the synthesis temperature at not less than 170° C. from the standpoint of preventing a decrease in the reaction rate of urea formation. It is preferable to set the synthesis temperature at not more than 210° C. from the standpoint of preventing a rise in the risk of what is called active corrosion in addition to an increase in the corrosion rate.

The N/C in the synthesis reactor is preferably not less than 3.0 from the standpoint of the equilibrium synthesis rate and preferably not more than 4.5 from the standpoint of preventing a gaseous phase from becoming apt to be formed due to a rise in the ammonia vapor pressure.

As shown in Formula 1 and Formula 2 above, the stoichiometric ratio of ammonia to carbon dioxide (N/C) in the synthesis of urea is 2. In actuality, however, in order to raise the urea equilibrium synthesis rate, it is preferred that excessive ammonia be supplied and that excessive unreacted ammonia be present.

From the standpoint of the urea synthesis rate, H/C is preferably not more than 1.0, and more preferably not more than 0.7. H/C may be zero. However, H/C is often determined, in the recovery apparatus (not shown in FIG. 1) for recovering unreacted substances (ammonia and carbon dioxide) which leave the apparatus for synthesizing urea, by the amount of the water necessary for the absorption of the unreacted substances and in actuality a certain amount of water is often present. H/C may be set at not less than 0.4, for example.

It is preferable to set the residence time of the process fluid in the synthesis reactor is not less than 10 minutes from the standpoint of causing the urea synthesizing reaction to proceed. Even when the residence time exceeds 40 minutes, the synthesis rate has already reached a level close to an equilibrium synthesis rate and a further increase in the synthesis rate is scarcely expected. Therefore, the residence time is preferably not more than 40 minutes.

Urea is synthesized in the condenser B and in the synthesis reactor A and an effluent substance 4 containing urea, which has left the synthesis reactor A, is supplied to the stripper C. In the effluent substance 4 at the outlet of the synthesis reactor A, synthesized urea, water, carbamate and unreacted ammonia are present as liquid phases and portions of unreacted ammonia and carbon dioxide are present as gaseous phases together with inert gases.

The inert gases here are a generic term for impurities contained in raw material carbon dioxide, such as hydrogen and nitrogen, and air introduced to prevent the corrosion of the apparatus for synthesizing urea, which is constituted by, for example, the synthesis reactor, the stripper, the condenser, the scrubber, the piping which connects them and the like.

The effluent substance 4 from the synthesis reactor A, which has been supplied to the stripper C, is heated by steam for heating 15 and the carbamate contained in the effluent substance 4 from the synthesis reactor A is thermally decomposed. The unreacted ammonia and unreacted carbon dioxide in the effluent substance from the synthesis reactor A are subjected to $CO_2$ stripping by the supplied raw material carbon dioxide 2a, and separated into gaseous components 5 containing carbon dioxide, ammonia and inert gases and a synthesis solution 10. The urea concentration of this synthesis solution is usually not less than 40 mass % but not more than 60 mass %.

Stripping refers to an operation which involves releasing, from the liquid, dissolved components in a solution by heating and/or by contact with a stripping agent (usually, a gas which is not dissolved or is not easily dissolved in the solution) and separating the dissolved components as gaseous phases.

The stripper C has a shell and tube heat exchange structure. On the shell side, steam for heating 15 is supplied and condensed water 16 which is condensation of this steam is discharged. The effluent substance from the synthesis reactor A is heated while passing the tube side. As described above, to perform both the stripping by heating and the stripping by carbon dioxide is preferable, because this not only is excellent in the stripping effect, but also is effective in decomposing carbamate. Incidentally, because the stripper C has also the function of gas-liquid separation, it is unnecessary to separately provide a gas-liquid separator which performs the gas-liquid separation of the effluent substance 4 from the synthesis reactor A.

The gaseous components 5 from the stripper are supplied to the condenser. On the other hand, the synthesis solution 10 from the stripper is fed to a decomposition apparatus (not shown in FIG. 1) and urea components are further refined.

An absorbing medium is supplied to the scrubber D. The recovered liquid 11 which is recovered in the recovery apparatus (not shown in FIG. 1) is used as this absorbing medium. The recovery apparatus and the recovered liquid will be described later in detail. Incidentally, in a case where the recovered liquid is returned from the recovery apparatus to the apparatus for synthesizing urea and used as the absorbing medium, this recovered liquid is called a recycled carbamate liquid.

The scrubber D is here provided in the interior of the condenser B, particularly in a gas-phase section in the upper part of the condenser. By providing the gas-phase section in the upper part of the condenser, gas-liquid separation is performed inside the condenser. In some cases, the gas-phase section may not be provided inside the condenser, and the scrubber and the gas-liquid separator may be arranged outside the condenser, whereby a similar function is carried out.

Here, the above-described recycled carbamate liquid 11 is supplied to the scrubber D as the absorbing medium. In the scrubber, the recycled carbamate liquid 11 is subjected to gas-liquid separation within the condenser, comes into contact with gaseous components which ascend from the gas-liquid interface, absorbs portions of the ammonia and carbon dioxide contained in this gaseous components, passes through the down pipe and is supplied to the lower part of the condenser. Ammonia, carbon dioxide and inert gases which have not been absorbed in the recycled carbamate liquid 11 are fed to the recovery apparatus through a line 12.

The line 12 through which gases discharged from the scrubber D flow is provided with a regulating valve (not shown in the figure) for adjusting the pressure of the apparatus for synthesizing urea. In the present invention, it is possible to perform the control of the apparatus for synthesizing urea with good response by providing a density meter in the synthesis solution line at the outlet of the condenser B, and therefore, the operation of the condenser becomes stable, with the result that it is possible to easily stabilize also the pressure control by the above-described regulating valve.

Scrubbing refers to an operation of cleaning a gas by bringing the gas into contact with a liquid and thereby absorbing a certain component in the gas in the liquid.

It is preferred that the condenser be operated at a pressure of not less than 13 MPaG but not more than 25 MPaG, at a temperature of not less than 160° C. but not more than 200° C., at N/C of not less than 2.5 but not more than 4.0, at H/C of not more than 1.0, and for a residence time of not less than 10 minutes but not more than 30 minutes.

The N/C in the condenser B is closely related to the N/C in the synthesis reactor. That is, the composition of the gas 5 at the outlet of the stripper is almost determined by the N/C of the synthesis reactor, and the N/C in the condenser is also determined. If the N/C in the condenser is determined, the N/C in the synthesis reactor is also determined. The H/C in the condenser is determined, in the recovery apparatus for recovering unreacted substances (ammonia and carbon dioxide) which leave the apparatus for synthesizing urea, by the amount of the water necessary for the absorption of the unreacted substances.

The condensation section and the stripper are operated at practically the same pressure as with the synthesis reactor.

The temperature of the process fluid within the condenser is preferably not less than 160° C. from the standpoint of the reaction rate of urea formation and preferably not more than 200° C. from the standpoint of suppressing a decrease in the condensation rate resulting from increase in the vapor pressure and the corrosion of the equipment materials.

The N/C of the process fluid within the condenser is preferably not less than 2.5 from the standpoint of suppressing a decrease in the condensation rate due to a rise in the partial pressure of carbon dioxide of the urea synthesis solution, and preferably not more than 4.0 from the standpoint of suppressing a decrease in the condensation rate due to a rise in the vapor pressure of ammonia.

From the standpoint of the urea synthesis rate, H/C is preferably not more than 1.0.

From the standpoint of suppressing a rise in the vapor pressure due to a decrease in the urea synthesis rate and a decrease in the condensation rate, the residence time within the condenser is preferably not less than 10 minutes. Even when the residence time exceeds 30 minutes, a remarkable increase in the urea synthesis rate cannot be expected. Therefore, the residence time is preferably not more than 30 minutes. The recycled carbamate liquid 11 which has absorbed part of the gaseous components supplied to the scrubber D via the condenser from the stripper C is supplied to the lower part of the condenser through the down pipe provided inside the condenser. In the condenser, this carbamate liquid and the gaseous components 5 come into contact with each other, ammonia and carbon dioxide are absorbed in the carbamate liquid and are condensed, and further, urea is formed by the carbamate forming reaction shown in Formula 1 and the dehydration reaction of carbamate shown by Formula 2.

The conversion ratio based on carbon dioxide in the condenser is usually not less than 20% but not more than 60%.

The ammonia and carbon dioxide which have not been condensed in the condenser, along with inert gases, are separated in the top section of the condenser or in the gas-liquid separator and fed to the recovery apparatus or the scrubber. Here, a gas mixture of them is separated in the top section of the condenser and further fed to the scrubber which is provided integrally with the condenser on top thereof.

On the other hand, the liquid 6 obtained by gas-liquid separation at the gas-liquid interface inside the condenser is supplied to the ejector E from the down pipe having an inlet below the gas-liquid interface inside the condenser, fed to the synthesis reactor by using the raw material ammonia as a driving source, and subjected to a further urea synthesizing reaction.

Details of each of the component will be given below.

The synthesis reactor A is either a vertical type or a horizontal type and may have a baffle plate, a gas distributor and the like which are installed in the interior thereof. Furthermore, as required, it is possible to adopt a structure in which the synthesis reactor is constructed integrally with the condenser and the like. However, even when the synthesis reactor is constructed integrally with the condenser, the synthesis reactor and the condenser are partitioned by a partition plate or the like, and they are independent.

For the stripper, it is possible to appropriately adopt a structure capable of performing gas-liquid contact and/or a structure capable of decomposing the carbamate in the synthesis solution 4 and emitting dissolved gases by heating.

As shown in FIG. 1, the stripper can have, for example, a vertical shell and tube heat exchange structure. In this case, a heat medium such as steam is supplied to the shell side and the synthesis solution 4 is supplied to the tube side, whereby heat can be supplied from the shell side to the tube side. Besides such structure, it is also possible to use a plate tower and a packed tower as the stripper. A combination of these structures may also be adopted.

As the structure of the scrubber, it is possible to appropriately adopt a structure capable of scrubbing, and it is possible to adopt a packed tower in which packing is packed, a shell and tube structure, a plate tower, and a combination thereof. The scrubber is operated at practically the same pressure as with the synthesis reactor, and for the temperature, the scrubber is usually operated at temperatures of not less than 100° C. but not more than 180° C. In the scrubber, absorption heat is generated by the absorption of gases. It is possible to remove and recover the absorption heat by use of a cooling medium if a shell and tube structure is adopted.

As required, the scrubber may be built in the condenser or may be constructed integrally with the condenser.

It is only necessary that the condenser have a structure capable of condensing gaseous components and absorbing ammonia and carbon dioxide, and furthermore, the condenser may have a structure capable of promoting the urea synthesizing reaction by reaction Formulas 1 and 2. If the condenser is a vertical type, this provides the advantages that gases are apt to be uniformly dispersed within the condenser, that the installation area is small, and that it is easy to ensure a long residence time of gases. Also, because the urea synthesizing reaction occurs in a liquid phase, it is desired that a cooling pipe be inserted into the liquid. Therefore, a vertical submerged condenser is preferable.

As the condenser, it is possible to adopt a structure in which a U-tube is installed as cooling means, for example, as shown in FIG. 1. This structure is suitable for a submerged condenser. That is, it is easy to ensure that the U-tube is brought into a condition in which the U-tube is completely immersed in a liquid phase. On the tube side, it is possible to supply a cooling medium such as boiler water. Or, by causing a process fluid, such as liquid ammonia and urea liquid, to flow as a cooling medium, it is possible to perform the preheating or heating of the process fluid at the same time with the cooling of the shell side fluid.

If a U-tube is used, only one tubesheet is sufficient. This is effective in weight saving.

As required, the condenser may be constructed integrally with the synthesis reactor.

The raw material ammonia 1a, which has been pressurized, and the liquid 6 obtained from the condenser are supplied to the ejector E, and the mixed fluid 8 of these liquids is supplied to the lower part of the synthesis reactor A. A portion 2b of the raw material carbon dioxide, which has been pressurized and which contains air (which air is supplied, for example, from the intermediate stage of a carbon dioxide compressor not shown in the figure), is supplied to the synthesis reactor. These supplied raw materials ascend inside the synthesis reactor and reactions according to reaction Formulas 1 and 2 occur during this time inside the synthesis reactor to form urea and the like. It is preferred that inside the synthesis reactor, a baffle plate be installed in order to promote mixing and reactions. The synthesis solution 4 in which the reactions have preferably reached an equilibrium is supplied from the upper part of the synthesis reactor A to the upper part of the stripper C. The raw material carbon dioxide 2a, which has been pressurized, is supplied from the lower part of the stripper C and performs the stripping of the unreacted ammonia and decomposition products of carbamate contained in the synthesis solution 4.

The stripper C shown in FIG. 1 has a vertical shell and tube type heat exchange structure. On the tube side, due to countercurrent contact between the synthesis solution 4 from the synthesis reactor A and the raw material carbon dioxide 2a, the unreacted substance (carbamate) in the synthesis solution 4 and excessive ammonium are stripped as gaseous components (ammonia and carbon dioxide). Steam 15 is supplied to the shell side of the stripper C and used as a heat source for the decomposition of carbamate. The gaseous components 5 from the upper part of the stripper C are supplied to the lower part of the condenser B. Also the recycled carbamate liquid from the scrubber D is supplied to the lower part of the condenser through the down pipe provided inside the condenser.

A U-tube as cooling means is installed inside the condenser B, water for cooling (boiler water) 13 is supplied to the U-tube, and a fluid 14 used in the cooling (a mixed fluid of boiler water and steam) is discharged from the U-tube.

The recycled carbamate liquid, which had been supplied as an absorbing medium to the shell portion of the condenser and has left the down pipe, and the gaseous components 5 from the stripper come into contact with each other while ascending within the condenser and are cooled, gaseous components are condensed and absorbed in the recycled carbamate liquid, ammonium carbamate is formed, and this causes the urea synthesizing reaction to occur.

Incidentally, the urea synthesis solution obtained in the synthesis reactor may be subjected to gas-liquid separation in the top section of the synthesis reactor. Or alternatively, without providing gas-liquid separation means inside the synthesis reactor, the urea synthesis solution is supplied to the stripper as is in a gas-liquid mixed phase.

It is possible to use a process computer as the calculating means for calculating an N/C value of the urea synthesis solution from measured values of the temperature and density of the liquid 6 and a second calculating means for calculating the flow rate of an ammonia component supplied to the synthesis reactor using the N/C value of the urea synthesis solution and for calculating the flow rate of the raw material ammonia so that the flow rate of the ammonia component becomes a flow rate which corresponds to a predetermined N/C value. For example, the data on density, temperature and the like is sent to one process computer installed in a central control room by use of an optical fiber via a distributed control system, a signal converter and the like, N/C is calculated in this process computer, the flow rate of the ammonia component supplied to the synthesis reactor is calculated, whereby it is possible to calculate the flow rate of the raw material ammonia which is such that the flow rate of the ammonia component supplied to the synthesis reactor becomes a flow rate corresponding to a predetermined N/C value. On the basis of the amount of this raw material ammonia, it is possible to adjust the opening of the flow rate regulating valve provided in the line which supplies the raw material ammonia to the synthesis reactor.

Now a description will be given of a method of calculating the N/C of the urea synthesis solution in the synthesis reactor by using the temperature and density of the liquid at the outlet of the condenser.

First, the N/C at the outlet of the condenser is found. The N/C at the outlet of the condenser (in the line 6 in FIG. 1), i.e., $(N/C)_{Cout}$, is a function of the density d ($kg/m^3$) and temperature t (°C.) of the liquid at the outlet of the condenser as given by the following formula.

$$(N/C)_{Cout}=c_1 d+c_2 t+c_3$$

The $c_1$, $c_2$ and $c_3$ in this formula can be found, for example, by the method of least squares by use of values of N/C and actual measurement values of temperature and density at not less than three points which are different from one another.

It becomes possible to get to know the N/C at the outlet of the condenser online simply by monitoring the density and temperature by use of this correlation.

Next, the mass flow rate (t/h) of the carbon dioxide component at the outlet of the condenser is found. Because the mass flow rate of the carbon dioxide component at the outlet of the condenser at a plant load of 100%, $F_{CO2,Cout,100\%}$ (t/h), is determined by a simulation or design material balance, the mass flow rate of the carbon dioxide component at the outlet of the condenser at an arbitrary plant load, $F_{CO2,Cout}$ (t/h), is found in a simplified manner by the following equation. In this formula, $P_L$ is a plant load (%). A plant load is the ratio of an actual amount of production to a design amount of production. The plant load may be found in a simplified manner as the ratio of an actual flow rate of the raw material carbon dioxide to a flow rate of the raw material carbon dioxide at a load of 100%.

$$F_{CO2,Cout}=F_{CO2,Cout,100\%} \times P_L/100$$

Next, the mass flow rate of the ammonia components at the outlet of the condenser, $F_{NH3,Cout}$ (t/h), is found from the following formula.

$$F_{NH3,Cout}=F_{CO2,Cout} \times (N/C)_{Cout}$$

In the embodiment shown in FIG. 1, the ammonia component supplied to the synthesis reactor A include the raw material ammonia 1a supplied to the ejector E in addition to the ammonia component contained in the liquid at the outlet of the condenser B, and the carbon dioxide component supplied to the synthesis reactor A include the raw material carbon dioxide 2b in addition to the carbon dioxide component included in the liquid at the outlet of the condenser B. Therefore, the mass flow rate of the ammonia components supplied to the synthesis reactor A, $F_{NH3,R}$ (t/h), the mass flow rate of the carbon dioxide components supplied to the synthesis reactor, $F_{CO2,R}$ (t/h), and the N/C in the synthesis reactor, i.e., $(N/C)_R$, are found from the following formulas. Here, $MW_{CO2}$ is the molecular weight of carbon dioxide and $MW_{NH3}$ is the molecular weight of ammonia.

$$F_{NH3,R}=F_{NH3,out}+\text{(mass flow rate of the raw material ammonia supplied to the ejector)}$$

$$F_{CO2,R}=F_{CO2,Cout}+\text{(mass flow rate of the raw material carbon dioxide supplied to the synthesis reactor)}$$

$$(N/C)_R(F_{NH3,R}/F_{CO2,R}) \times (MW_{CO2}/MW_{NH3})$$

The N/C in the synthesis reactor is found in the above-described manner

Next, a description will be given of a method of controlling the N/C in the synthesis reactor to a target value. If a target N/C is expressed by $N/C_{R,O}$, then the N/C in the synthesis reactor becomes this target value when the mass flow rate of the ammonia components supplied to the synthesis reactor is $F_{NH3,R,O}$, which is expressed by the following formula.

$$F_{NH3,R,O}=(N/C)_{R,O} \times F_{CO2,R} \times (MW_{NH3}/MW_{CO2})$$

Therefore, it is possible to make the N/C in the synthesis reactor be $(N/C)_{R,O}$ by adjusting the amount of the raw material ammonia 1a so that the ammonia components supplied to the synthesis reactor become $F_{NH3,R,O}$.

Also, by measuring the mass flow rate of the recycled carbamate (in the line 11) fed from the recovery apparatus to the apparatus for synthesizing urea, it is possible to find the mass flow rate of the water components, $F_{H2O,Cout}$ (t/h), at the outlet of the condenser and it is also possible to calculate the material balance of the whole apparatus for synthesizing urea, which has the synthesis reactor, the stripper and the condenser.

The H/C at the outlet of the condenser, i.e., $(H/C)_{Cout}$ is found by the following formula. In this formula, $F_{RC}$ is the mass flow rate (t/h) of the recycled carbamate (in the line 11). And $c_4$ and $c_5$ can be determined by measured material balance or design material balance (simulation). For example, they can be found by the method of least squares by use of values of H/C and actual measurement values of $F_{RC}$ at not less than two points which are different from each other.

$$(H/C)_{cout}=c_4(F_{RC}/P_L)+c_5$$

Therefore, the mass flow rate of the water component at the outlet of the condenser is found as follows.

$$F_{H2O,Cout}=F_{CO2,Cout} \times (H/C)_{Cout}$$

In the embodiment shown in FIG. 1, the water component supplied to the synthesis reactor A are only the water component contained in the liquid at the outlet of the condenser and, therefore, the flow rate of the water component supplied to the synthesis reactor is also $F_{H2O,Cout}$. In the synthesis reactor A, there is no increase or decrease in the ammonia component, carbon dioxide component and water component.

Figure 5:
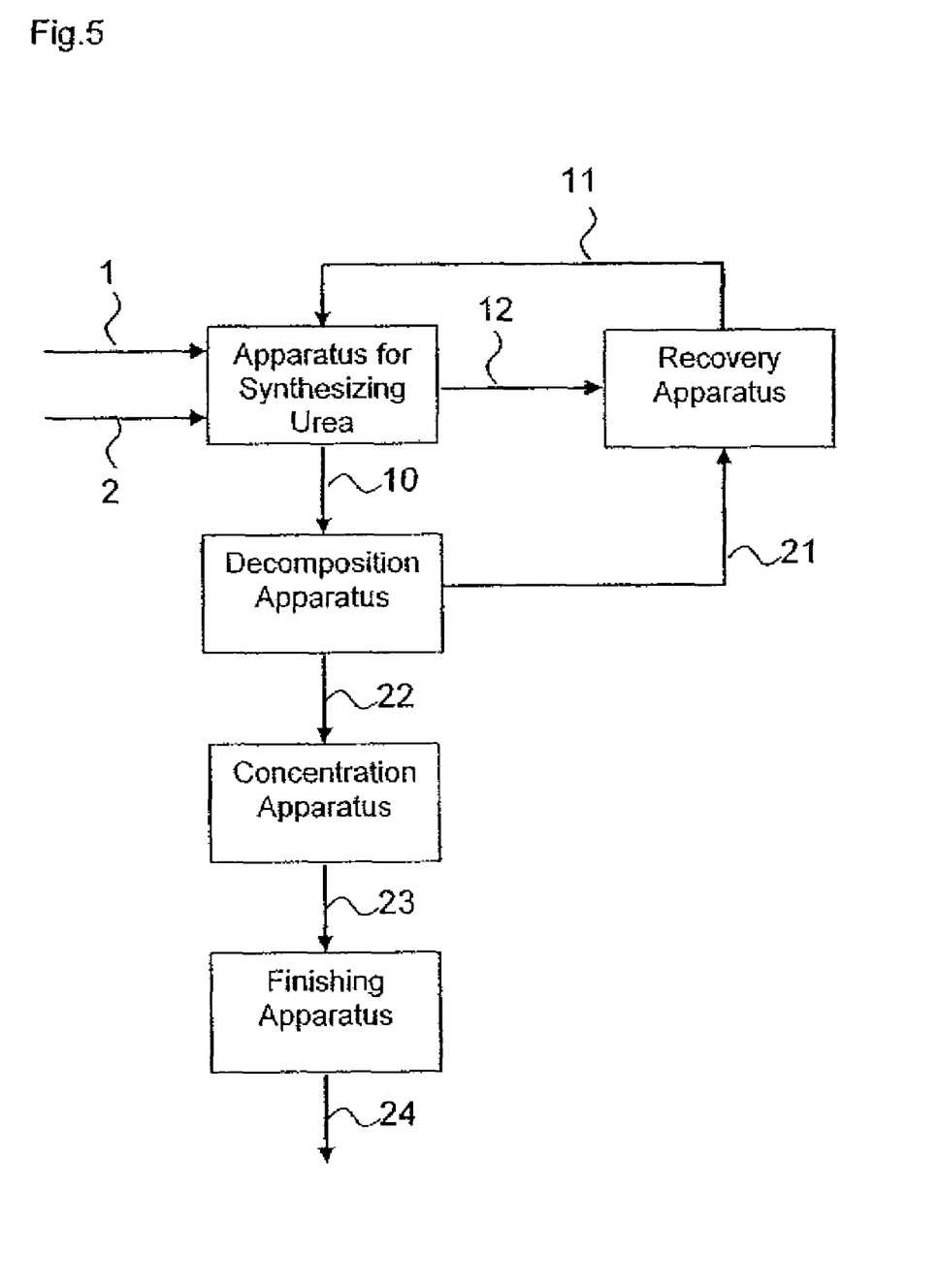
FIG. 5 is a flow diagram to explain a urea production plant.

Now a description will be given of an example of a urea production plant including an apparatus for synthesizing urea. An outline of the urea production plant is shown in FIG. 5. The urea production plant has an apparatus for synthesizing urea, a recovery apparatus, a decomposition apparatus, a concentration apparatus and a finishing apparatus. The raw material ammonia 1 and the raw material carbon dioxide 2 are supplied to the apparatus for synthesizing urea. The urea synthesis solution 10 which has undergone stripping is fed from the apparatus for synthesizing urea to the decomposition apparatus.

In the decomposition apparatus, by heating the supplied urea synthesis solution under reduced pressure, the unreacted ammonia and carbamate contained in the urea synthesis solution are vaporized and decomposed respectively, and separated as a gas 21 containing ammonia and carbon dioxide. The remaining liquid phase becomes an aqueous solution of urea 22 in an amount of 68 mass % or so, for example, and fed to the concentration apparatus downstream of the decomposition apparatus.

In the concentration apparatus, by heating under vacuum the aqueous solution of urea 22 obtained in the decomposition apparatus, the moisture is almost completely evaporated and separated, and molten urea 23 of 99.7 mass % or so, for example, is obtained. This molten urea is fed to the finishing apparatus downstream of the concentration apparatus, where the molten urea is cooled and solidified, and finished as granular urea 24.

On the other hand, the gas 21 containing ammonia and carbon dioxide which has been separated in the decomposition apparatus and the gas 12 containing ammonia, carbon dioxide and inert gases come into contact with water in the recovery apparatus. As a result of this, the ammonia and carbon dioxide contained in these gases are absorbed in the water and a recovered liquid, which is an aqueous solution of ammonium carbamate, is recovered. This recovered liquid is pressurized and then returned to the apparatus for synthesizing urea as the recycled carbamate liquid 11.

Figure 2:
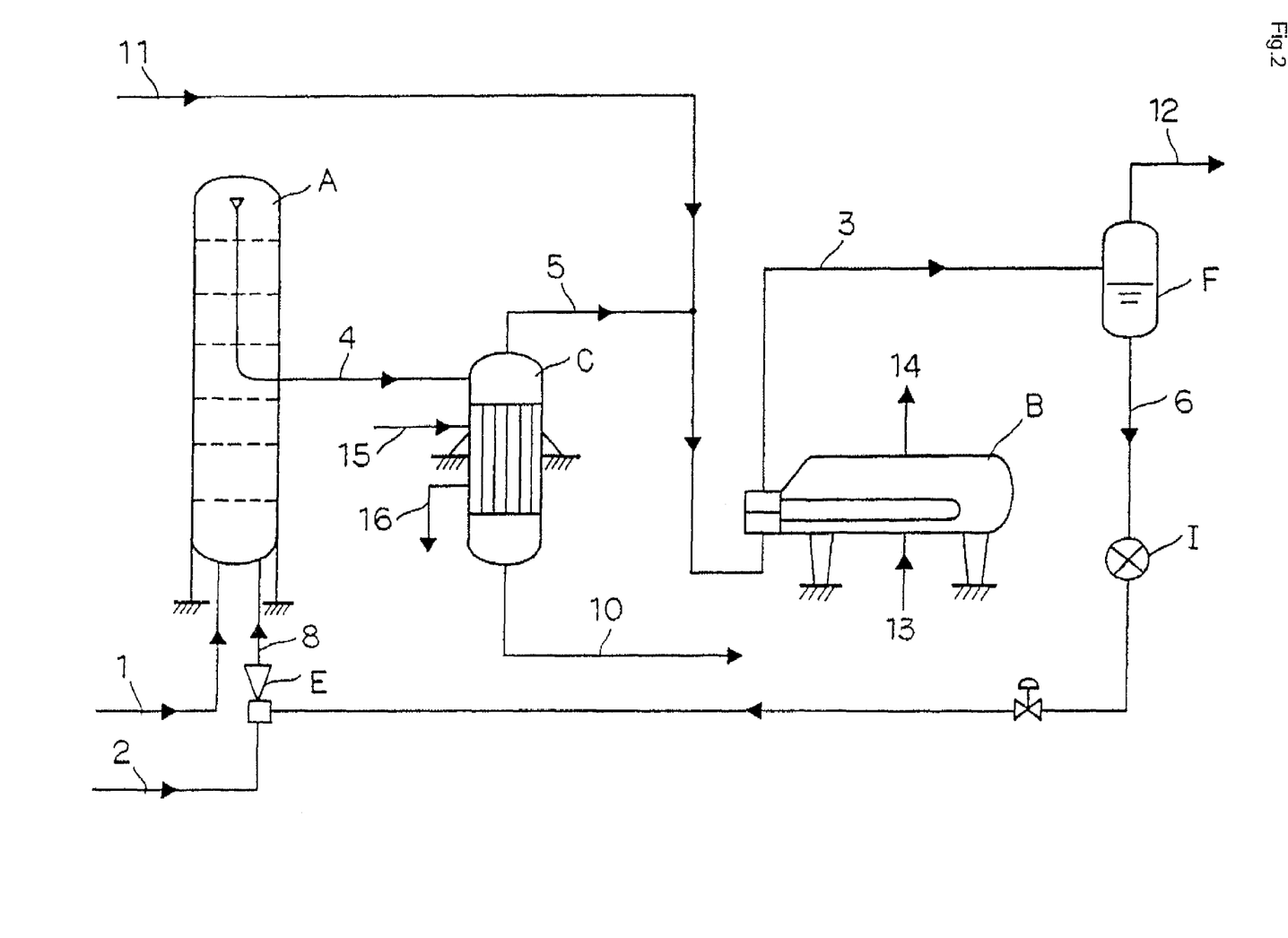
FIG. 2 is a flow diagram which illustrates another embodiment of an apparatus for synthesizing urea of the present invention.

Another embodiment of the present invention is shown in FIG. 2. In this embodiment, a condenser B is a horizontal type and the condenser has a shell and tube structure, and the process fluid flows on the tube side and the cooling medium flows on the shell side. The residence time of the process fluid in the condenser is short and a reaction scarcely occurs in this condenser. Carbon dioxide is not supplied to a stripper, and the stripping of a synthesis solution 4 is performed by the heating by a heating medium 15.

Raw material carbon dioxide 2 is supplied to the bottom of a synthesis reactor A. Raw material liquid ammonia 1 aspirates a liquid 6 obtained from the condenser by use of an ejector E, and a mixed fluid of them is supplied to the bottom of the synthesis reactor A. A synthesis solution 4 obtained in the synthesis reactor passes through a down pipe having an opening near the top inside the synthesis reactor A and is supplied to the stripper C. The stripper C has a shell and tube structure. Steam for heating 15, which is a heating medium, flows on the shell side and condensed water 16 thereof is discharged. On the other hand, the synthesis solution 4 is heated and gaseous components 5 are separated from the top and a synthesis solution 10 which remains is fed to a decomposition apparatus, which is not shown in FIG. 2. The gaseous components 5 are mixed with a recycled carbonate liquid 11 and supplied to the condenser B, where the mixture is cooled by a cooling medium 13 and uncondensed portions are condensed. A carbamate liquid 3 which has passed through the condenser is subjected to gas-liquid separation by the gas-liquid separator F, gaseous components 12 are fed to a recovery apparatus, which is not shown in FIG. 2, and the liquid components 6 are supplied to the ejector E.

The density of the liquid components 6 obtained from the condenser is measured online by use of a density meter I. The temperature of this liquid is also measured online by a thermometer not shown in the figure. The calculation of N/C, the calculation of the amount of ammonia held in the synthesis reactor, and the adjustment of the amount of ammonia supplied to the synthesis reactor can be performed in the same manner as in the embodiment shown in FIG. 1.

Figure 3:
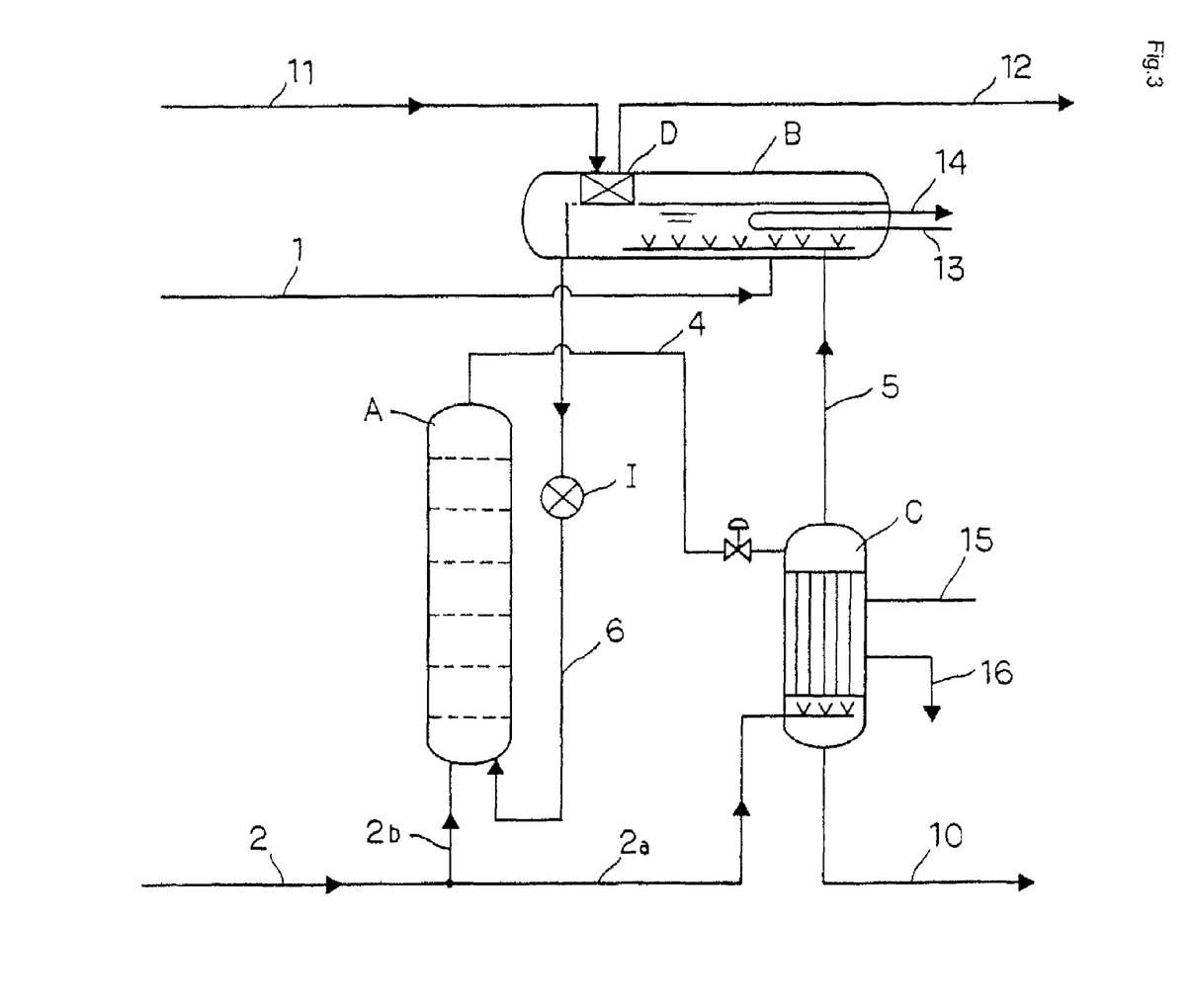
FIG. 3 is a flow diagram which illustrates a further embodiment of an apparatus for synthesizing urea of the present invention.

A further embodiment of the present invention is shown in FIG. 3. In this embodiment, a condenser B is a horizontal submerged condenser in which a scrubber D is built. The condenser is provided in a position higher than a synthesis reactor A, the recycling of a liquid from the condenser to the synthesis reactor is performed by using gravity, and pressurizing means such as an ejector is not used.

A portion 2b of raw material carbon dioxide 2 and a liquid 6 obtained from the condenser are supplied to the bottom of the synthesis reactor A. A synthesis solution 4 obtained in the synthesis reactor A is supplied to a stripper C and stripped by the remaining portion 2a of the raw material carbon oxide and by the heating by a heating medium. Gaseous components 5 are supplied from the top of the stripper to the condenser, and the remaining portion of a synthesis solution 10 is supplied to a decomposition apparatus, which is not shown in FIG. 3. A regulating valve for the adjustment of the liquid level of the condenser B is provided in a line through which the synthesis solution 4 flows, between the synthesis reactor A and the stripper C. The gaseous components 5 and raw material ammonia 1 are supplied to the condenser B, and a recycled carbamate liquid 11 is supplied to the condenser via the scrubber D. Inside the condenser, a U-tube through which a cooling medium flows is provided horizontally. Gaseous components 5 are cooled and condensed, in the scrubber D uncondensed gases are further absorbed in the recycled carbamate liquid, and gaseous components 12 which finally remain are fed to a recovery apparatus, which is not shown in FIG. 3. On the other hand, the liquid component 6 is recycled to the synthesis reactor.

The density of the liquid components 6 obtained from the condenser B is measured online by use of the density meter I. The temperature of this liquid is also measured online by a thermometer not shown in the figure. The calculation of N/C, the calculation of the amount of ammonia held in the synthesis reactor, and the adjustment of the amount of ammonia supplied to the synthesis reactor can be performed in the same manner as in the embodiment shown in FIG. 1.

Figure 4:
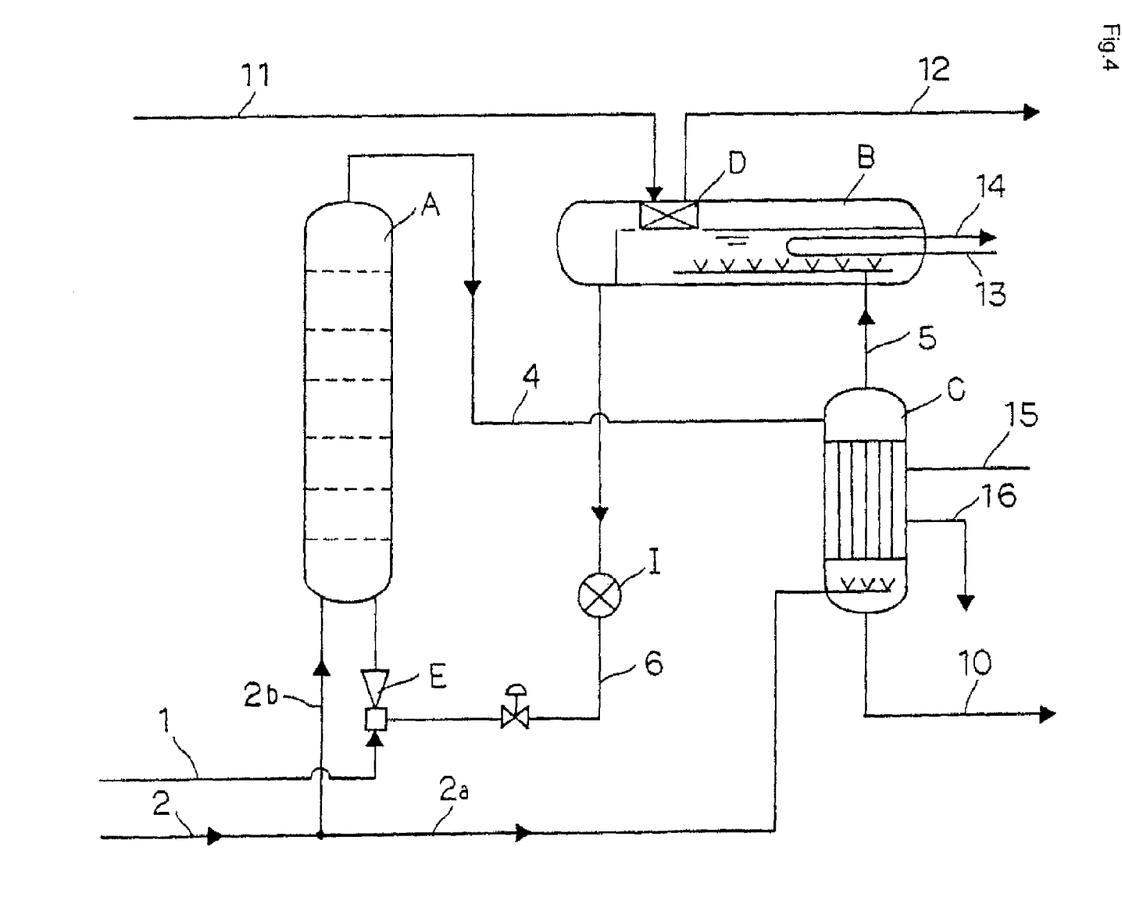
FIG. 4 is a flow diagram which illustrates a still further embodiment of an apparatus for synthesizing urea of the present invention.

A still further embodiment of the present invention is shown in FIG. 4. In this embodiment, a condenser B is provided in a somewhat low position compared to the embodiment shown in FIG. 3, and the height of the top end of a synthesis reactor is almost the same as the height of the top end of the condenser B (it is also possible that the top end of the condenser is lower than the top end of the synthesis reactor). An ejector E is used to recycle a condensed liquid 6 to the synthesis reactor, and raw material ammonia 1 aspirates the condensed liquid 6 in the ejector and enters the synthesis reactor A. A regulating valve is provided in a line 6 in order to adjust the liquid level of the condenser B.

EXAMPLES

The present invention will be described below in further detail by an example. However, the present invention is not limited thereby.

Example 1

Table 1 shows the material balance, temperatures and pressures at a rating, i.e., at a plant load of 100% in an example of production of 1725 t/day of urea when the apparatus for synthesizing urea of the embodiment shown in FIG. 1 is used. In Table 1, ammonium carbamate is shown as ammonia and carbon dioxide.

Out of the raw material ammonia 1 at a pressure of 23 MPaG and a temperature of 30° C., 39.7 t/h were heated by the heat exchanger G to 140° C. and then supplied to the ejector E via the line 1a and 1.0 t/h was supplied to the condenser B via the line 1b. On the other hand, carbon dioxide 2 at a pressure of 0.1 MPaG and a temperature of 40° C. was pressurized by a compressor (not shown in the figure) and carbon dioxide at a pressure of 16 MPaG and a temperature of 120° C. was obtained. And 41.2 t/h of this carbon dioxide were supplied to the stripper C through the line 2a and 9.1 t/h were supplied to the synthesis reactor A through the line 2b to produce urea.

The supplied ammonia 1a was mixed in the ejector E with the synthesis solution 6 at a pressure of 15.2 MPaG from the condenser B, and supplied at a pressure of 15.5 MPaG from the line 8 to the synthesis reactor A.

The synthesis reactor A was operated at a pressure of 15.5 MPaG, at a temperature of 182° C., at N/C of 3.7, at H/C of 0.58 and for a residence time of 20 minutes, and urea was synthesized. The conversion ratio based on carbon dioxide in the synthesis reactor was 63%.

The synthesis solution 4 containing urea from the upper part of the synthesis reactor A was supplied to the stripper C. Medium-pressure steam 15 was supplied to the shell side of the stripper C to supply heat for the decomposition of carbamate and went out as condensed water 16. On the tube side of the stripper C, the decomposition of carbamate and stripping were performed at an upper part temperature of 184° C., at a lower part temperature of 171° C., and at a pressure of 15.5 MPaG, and gaseous components were separated in the upper part. The gaseous components 5 were fed to the condenser B, and the synthesis solution 10 which had left the bottom of the stripper C was fed to the decomposition apparatus.

Then, 134.6 t/h of the gaseous components from the stripper C (in the line 5) and 62.2 t/h of the recycled carbamate liquid (in the line 11) were fed to the condenser B. The condenser B was operated at a temperature of 180° C., at a pressure of 15.2 MPaG, at N/C of 2.9, at H/C of 0.65, and for a residence time of 20 minutes, and urea and the like were synthesized. The conversion ratio based on carbon dioxide in the condenser was 46%.

The density of the condensed liquid was measured by use of a radiation type density meter I (made by Ohmart Corporation, trade name: DENSART D-3000) installed in the line 6. The density of the condensed liquid was 1025 kg/m$^3$. The temperature of the condensed liquid during the density measurement was 180° C. Other operating conditions are shown in Table 1.

From the liquid amount of the recycled carbamate and the simplified formula of a plant load, the H/C of the condensed liquid 6 was estimated at 0.65. The flow rate of the fluid at the outlet of the condenser was calculated. As a result, the flow rate of the ammonia component was 91.1 t/h, the flow rate of the carbon dioxide component was 81.2 t/h, and the flow rate of the water component was 21.5 t/h. In this calculation, it was assumed that the flow rate of the carbon dioxide component is the same as that in the material balance at a 100% load.

A calculation to raise the N/C of the fluid at the outlet of the condenser to 3.0 was performed. An ammonia component in an amount of $(81.2/44) \times 3.0 \times 17 = 94.1$ (t/h) is necessary.

Therefore, it is only necessary that the amount of ammonia be increased by 94.1−91.1=3.0 t/h. The amount of the raw material ammonia was increased from 40.7 t/h to 43.7 t/h, with the result that in 40 minutes, the N/C in the condenser rose to 3.0. As a result, the N/C in the synthesis reactor was able to be raised from 3.7 to 3.8.

A process and an apparatus for synthesizing urea of the present invention can each be favorably used in a process and an apparatus for synthesizing urea which manufacture urea from ammonia and carbon dioxide.

TABLE 1

| | | Line No. | | | | | | | | | | | | |
|---|---|---|---|---|---|---|---|---|---|---|---|---|---|---|
| | | 1 | 1a | 1b | 2 | 2a | 2b | 2c | 4 | 5 | 6 | 8 | 10 | 11 | 12 |
| Urea | t/h | | | | | | | | 77.3 | | 50.8 | 50.8 | 73.5 | 0.3 | |
| Ammonia | t/h | 40.7 | 39.7 | 1.0 | | | | | 86.9 | 69.7 | 62.3 | 102.0 | 19.2 | 21.9 | 1.6 |
| Carbon Dioxide | t/h | | | | 52.7 | 41.2 | 9.1 | 2.4 | 33.6 | 58.5 | 43.9 | 43.9 | 18.9 | 24.7 | 2.2 |
| Water | t/h | | | | | | | | 44.6 | 6.4 | 36.7 | 36.7 | 37.2 | 15.3 | 0.2 |
| Total | t/h | 40.7 | 39.7 | 1.0 | 52.7 | 41.2 | 9.1 | 2.4 | 242.4 | 134.6 | 193.7 | 233.4 | 148.8 | 62.2 | 4.0 |
| Temperature | ° C. | 30 | 140 | 30 | 40 | 120 | 120 | 150 | 182 | 184 | 180 | 170 | 171 | 105 | 160 |
| Pressure | MPaG | 23.0 | 23.0 | 23.0 | 0.1 | 16.0 | 16.0 | 0.5 | 15.5 | 15.5 | 15.2 | 15.5 | 15.5 | 16.0 | 15.2 |
| N/C | mol/mol | | | | | | | | 3.7 | | 2.9 | | | | |
| H/C | mol/mol | | | | | | | | 0.58 | | 0.65 | | | | |
| CO2 Conversion Ratio | % | | | | | | | | 63 | | 46 | | | | |

The invention claimed is:

1. A method for synthesizing urea, comprising:
   obtaining a urea synthesis solution which contains urea, unreacted ammonia, unreacted carbon dioxide and water;
   causing ammonia and carbon dioxide to react with each other;
   separating a gas mixture containing the unreacted ammonia and the unreacted carbon dioxide by stripping the urea synthesis solution using at least a part of raw material carbon dioxide;
   obtaining a condensed liquid by condensing the gas mixture in an absorbing medium while cooling the gas mixture;
   recycling the condensed liquid to the reaction step; and
   measuring the density of the condensed liquid online, using a noncontact type density meter.

2. The method according to claim 1, further comprising measuring the temperature of the condensed liquid online and determining an N/C value of the condensed liquid using measured values of the temperature and the density.

3. The method according to claim 2, further comprising calculating an N/C value of the urea synthesis solution using the N/C value of the condensed liquid.

4. The method according to claim 3, further comprising controlling the N/C value of the urea synthesis solution to a predetermined value by adjusting the flow rate of raw material ammonia and/or raw material carbon dioxide.

5. The method according to claim 1, wherein the noncontact type density meter is a radiation type density meter.

6. An apparatus for synthesizing urea, comprising:
   a synthesis reactor for obtaining a urea synthesis solution which contains urea, unreacted ammonia, unreacted carbon dioxide and water by causing ammonia and carbon dioxide to react with each other;
   a stripper for separating a gas mixture containing the unreacted ammonia and the unreacted carbon dioxide by stripping the urea synthesis solution using at least a part of raw material carbon dioxide;
   a condenser for obtaining a condensed liquid by condensing the gas mixture in an absorbing medium while cooling the gas mixture;
   a gas-liquid separator for removing gas from the condensed liquid,
   recycling means for recycling the condensed liquid to the synthesis reactor; and
   a noncontact type density meter for measuring the density of the condensed liquid online.

7. The apparatus for synthesizing urea according to claim 6, further comprising a thermometer for measuring the temperature of the condensed liquid online and calculating means for calculating an N/C value of the condensed liquid using measured values of the temperature and the density.

8. The apparatus according to claim 7, further comprising calculating means for calculating an N/C value in the synthesis reactor using the N/C value of the condensed liquid.

9. The apparatus according to claim 8, further comprising control means for controlling the N/C value in the synthesis reactor to a predetermined value by adjusting the flow rate of raw material ammonia and/or raw material carbon dioxide.

10. The apparatus according to claim 6, wherein the noncontact type density meter is a radiation type density meter.

11. The method according to claim 1, further comprising controlling operation conditions of reaction of the ammonia and the carbon dioxide using the measured density.

12. The method according to claim 11, further comprising monitoring online a temperature of the condensed liquid and determining a mole ratio of an ammonia component to a carbon dioxide component (N/C value) of the condensed liquid based on the monitored temperature and density, wherein the controlling step is performed using the N/C value.

13. The method according to claim 12, further comprising calculating an N/C value of the reaction using the N/C value of the condensed liquid.

14. The method according to claim 13, wherein the controlling step is performed by controlling the N/C value of the reaction at a predetermined value by adjusting a flow rate of raw material ammonia and/or a flow rate of raw material carbon dioxide.

15. The method according to claim 1, further comprising separating noncondensed gas from the condensed liquid prio to measuring the density thereof.

16. The method according to claim 1, wherein the noncontact type density meter is positioned along a stream of the condensed liquid on route to being recycled to the reaction step.

17. The method of claim 16, wherein no other noncontact type density meter is used in the method.

* * * * *

UNITED STATES PATENT AND TRADEMARK OFFICE
CERTIFICATE OF CORRECTION

| | |
|---|---|
| PATENT NO. | : 7,498,464 B2 |
| APPLICATION NO. | : 11/421002 |
| DATED | : March 3, 2009 |
| INVENTOR(S) | : Yasuhiko Kojima |

It is certified that error appears in the above-identified patent and that said Letters Patent is hereby corrected as shown below:

On the title page: Add Item --(30) Foreign Application Priority Data May 31, 2005 (JP), 2005-159030--.

Column 5, line 4; Change "NIC" to --N/C--.

Column 7, line 19; Change "1b" to --1*b*--.

Column 11, line 1-10; Delete "The recycled carbamate liquid 11 which has absorbed part of the gaseous components supplied to the scrubber D via the condenser from the stripper C is supplied to the lower part of the condenser through the down pipe provided inside the condenser. In the condenser, this carbamate liquid and the gaseous components 5 come into contact with each other, ammonia and carbon dioxide are absorbed in the carbamate liquid and are condensed, and further, urea is formed by the carbamate forming reaction shown in Formula 1 and the dehydration reaction of carbamate shown by Formula 2." and insert the same below "30 minutes." as a new paragraph.

Column 12, lines 52-57; After "decomposition of carbamate." delete "The gaseous components 5 from the upper part of the stripper C are supplied to the lower part of the condenser B. Also the recycled carbamate liquid from the scrubber D is supplied to the lower part of the condenser through the down pipe provided inside the condenser." and insert the same below "decomposition of carbamate." as a new paragraph.

UNITED STATES PATENT AND TRADEMARK OFFICE
CERTIFICATE OF CORRECTION

PATENT NO. : 7,498,464 B2
APPLICATION NO. : 11/421002
DATED : March 3, 2009
INVENTOR(S) : Yasuhiko Kojima It is certified that error appears in the above-identified patent and that said Letters Patent is hereby corrected as shown below:

Column 14, line 27; Change "$(N/C)_R(F_{NH3,R}/F_{CO2,R})x(MW_{CO2}/MW_{NH3})$" to --$(N/C)_R=(F_{NH3,R}/F_{CO2,R})x(MW_{CO2}/MW_{NH3})$--

Column 14, line 29; Change "manner" to --manner.--.

Column 14, line 50; Change "$(HIC)_{Cout}$" to --$(H/C)_{Cout}$--.

Column 14, line 59; Change "$(H/C)_{cout}$" to --$(H/C)_{Cout}$--.

Signed and Sealed this

Fourteenth Day of July, 2009

JOHN DOLL
*Acting Director of the United States Patent and Trademark Office*